United States Patent
Nhamias et al.

(10) Patent No.: US 9,849,097 B2
(45) Date of Patent: Dec. 26, 2017

(54) DOSAGE FORMS CONTAINING TERBUTALINE SULPHATE

(71) Applicant: Jagotec AG, Muttenz (CH)

(72) Inventors: Alain Nhamias, Bartenheim (FR); Nasser Beniou, Mulhouse (FR)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 14/433,241

(22) PCT Filed: Oct. 8, 2013

(86) PCT No.: PCT/EP2013/070900
§ 371 (c)(1),
(2) Date: Apr. 2, 2015

(87) PCT Pub. No.: WO2014/056882
PCT Pub. Date: Apr. 17, 2014

(65) Prior Publication Data
US 2015/0250742 A1    Sep. 10, 2015

(30) Foreign Application Priority Data
Oct. 8, 2012  (GB) .................................. 1218012.1

(51) Int. Cl.
A61K 31/137 (2006.01)
A61K 9/28 (2006.01)
A61K 45/06 (2006.01)
A61K 9/20 (2006.01)

(52) U.S. Cl.
CPC .......... *A61K 31/137* (2013.01); *A61K 9/2018* (2013.01); *A61K 9/2077* (2013.01); *A61K 9/2893* (2013.01); *A61K 45/06* (2013.01); *A61K 9/2813* (2013.01)

(58) Field of Classification Search
CPC .. A61K 31/137; A61K 31/138; A61K 9/2806; A61K 9/2866; A61K 9/2893; A61K 9/2077; A61K 9/2018
See application file for complete search history.

(56) References Cited

U.S. PATENT DOCUMENTS

2002/0015730 A1    2/2002  Hoffmann et al.

FOREIGN PATENT DOCUMENTS

| EP | 0257915 A1 | 3/1988 |
| WO | WO-2006/122021 A1 | 11/2006 |
| WO | WO-2008/038155 A2 | 4/2008 |
| WO | WO-2011/009818 A1 | 1/2011 |

OTHER PUBLICATIONS

International Search Report issued in PCT/EP2013/070900 dated Jan. 14, 2014.
Ranabir Chanda et al. "Formulation of terbutaline sulphate mucoadhesive sustained release oral tablets from natural materials and in vitro-in vivo evaluation." Asian Journal of Pharmaceutical Sciences. vol. 5 No. 4 (2010): pp. 168-174.

(Continued)

*Primary Examiner* — Lakshmi S Channavajjala
(74) *Attorney, Agent, or Firm* — Mintz Levin Cohn Ferris Glovsky and Popeo, P.C.; Muriel Liberto, Esq.

(57) ABSTRACT

A modified release oral dosage form comprising an internal phase containing terbutaline sulphate and a pharmaceutically acceptable excipient, dispersed in an external phase comprising pharmaceutically acceptable excipients.

27 Claims, 5 Drawing Sheets

(56) References Cited

OTHER PUBLICATIONS

Chanda R et al. "Formulation of oral mucoadhesive tablets of terbutaline sulphate using some natural materials and in vitro-in vivo evaluation," Journal of pharmaceutical research and health care. vol. 2 No. 1 (Jan. 2010): pp. 32-45.

Harish N M et al. "Formulation design and optimization of sustained release tablets of terbutaline sulphate," Indian journal of pharmaceutical education and research, associate of pharmaceutical teachers of India Ind, In. vol. 45 No. 3 (2011): pp. 259-266.

DOSAGE FORMS CONTAINING TERBUTALINE SULPHATE

CROSS-REFERENCE TO RELATED APPLICATIONS

This application is a U.S. national phase of PCT/EP2013/070900, filed Oct. 8, 2013, which claims the benefit of GB 1218012.1, filed Oct. 8, 2012, the contents of which are hereby incorporated by reference in their entireties.

The present invention is concerned with dosage forms containing terbutaline sulphate and their use in the treatment of nocturnal hypoglycaemia.

Currently marketed dosage forms of terbutaline sulphate are in the form of tablets at 2.5 mg and 5 mg dosage strengths, and a syrup at 0.3 mg/ml. Terbutaline sulphate is indicated for the relief of bronchospasm associated with chronic obstructive pulmonary disease for the prevention of and reversal of bronchospasm in patients 12 years of age and older with asthma and reversible bronchospasm associated with bronchitis and emphysema, and for the management of pre-term labour. It is a member of a class of substances called beta 2 adrenergic receptor agonists.

In a study reported in The Journal of Endocrinology and Metabolism 91(6): 2087-2092 2006, 5 mg terbutaline sulphate in immediate release tablet dosage form ("Brethine" Novartis) was investigated as a putative treatment for nocturnal hypoglycaemia in patients with type I diabetes. The tablets were administered without any other conventional treatments, e.g. snacks or the like. It was concluded that whereas the tablets prevented nocturnal hypoglycaemia over the full sleep period, unfortunately subjects developed hyperglycaemia upon wakening. It also raised heart rates and blood lactate concentrations.

The same "Brethine" immediate release tablets in lower dose (2.5 mg) were investigated in a study reported in Diabetes Care Vol. 31, No. 12, 2271-2272 December 2008. The effect of this lower dose suggested a dose proportional effect, as its impact on hypoglycaemia was intermediate between the 5 mg dose and no dose at all. However, the investigators were unable to confirm from the study if the lower dose prevented hyperglycaemia in subjects upon wakening.

A modified release oral dosage form containing terbutaline sulphate, and its use in the treatment of nocturnal hypoglycaemia in insulin treated diabetis patients is described in EP2456430.

The stability of a drug substance is an important factor in the manufacture of safe and effective pharmaceutical products. Stability studies are required to be submitted by any applicant seeking approval for a new pharmaceutical product. Stability study requirements are covered, for example in the United States Pharmacopea, in the Good Manufacturing Practices (GMP) as well as in FDA and ICH Guidelines.

It is known that many drugs exhibit poor or modest shelf stability. The presence of degradation products of these drugs can give rise to efficacy or toxicity issues, but even if they do not, the diminution of the concentration of a drug as a result of its degradation is inherently undesirable, as it make therapy with the drug less certain.

Stability issues can be caused by environmental factors such as humidity, temperature and the like. However, degradation may result from, or be accelerated by, interactions of drug substances with pharmaceutical excipients such as fillers, binders, lubricants, glidants and disintegrating agents or impurities contained in any of these excipients.

It is normal practice in the field of pharmaceuticals to formulate drug substances with multiple excipients for all manner of reasons. Often excipients are employed simply to give bulk to a pharmaceutical formulation where the drug substance is present in very small quantities, but particularly in the case of modified release dosage forms, they can be employed in order to influence how a drug is released from the dosage form to achieve a desired therapeutic outcome. Excipients are selected with the expectation that they are therapeutically and chemically inert, but sometimes they can participate in unpredictable chemical degradation reactions.

Thus, in the development of a terbutaline sulphate dosage form, the applicant carried out accelerated stability studies on the drug at a temperature of 60° C. and 90% relative humidity for up to 4 weeks. No degradation products were observed.

Subsequently, binary stability studies were carried out using mixtures of terbutaline sulphate and single excipients at 60° C. and 90% relative humidity for up to 5 weeks. Again, no degradation products could be detected, or levels of degradation product were below the limits of quantification according to the analytical method adopted.

The findings regarding the stability of terbutaline sulphate entirely to be expected, as terbutaline has been reported to be a highly stable drug substance that requires rather harsh reaction conditions before it is possible to detect any oxidative degradation products ("Stressed oxidative degradation of terbutaline in aqueous solutions—identification of the degradation products" Leif-åke Svensson Acta Pharma Suecica 9, 141-146, 1972)

Having regard to the results of these studies and what is known in the art, the applicant was surprised to find that when terbutaline sulphate was formulated with multiple excipients selected from those employed in the binary study, significant detectable levels of the degradation product terbutaline impurity B (a dihydro iso-quinoline derivative) were observed.

Furthermore, the use of anti-oxidants such as butylated hydroxytoluene (BHT) or sodium metabisulphite failed to abate the problem adequately.

There is a need to address this problem and provide a stable oral dosage form containing terbutaline sulphate.

The present invention addresses this problem and provides in a first aspect an oral dosage form containing terbutaline sulphate, comprising an internal phase comprising particles comprising a mixture of terbutaline sulphate and a pharmaceutically acceptable excipient, said particles being dispersed in an external phase comprising pharmaceutically acceptable excipients.

The invention provides in another of its aspects the use of an oral dosage form described herein in a method of treating nocturnal hypoglycaemia in a patient in need of treatment.

In another aspect of the invention there is provided the use of an oral dosage form described herein in a method of treating nocturnal hypoglycaemia in a patient in need of treatment, in particular without eliciting, or at least minimizing, adverse events such as incidences of hyperglycaemia in the treated patient upon wakening and/or worsening glucose control.

In still other aspects of the invention there is provided a method and a regimen for treating nocturnal hypoglycaemia in a patient in need of treatment.

In still another aspect of the present invention there is provided a method and a regimen for treating nocturnal hypoglycaemia in a patient in need of treatment, in particular without eliciting, or at least minimizing, adverse events such as incidences of hyperglycaemia in treated patients upon wakening and/or worsening glucose control.

In yet another aspect of the invention there is provided a method for stabilising an oral dosage form comprising terbutaline sulphate and pharmaceutically acceptable excipients, by preventing or limiting the exposure of terbutaline sulphate to contact with multiple excipients, said method comprising the steps of:— i) admixing terbutaline sulphate with a pharmaceutically acceptable excipient to form an internal phase comprising particles comprising terbutaline sulphate dispersed in a matrix of said excipient, and ii) mixing the particles of the internal phase with an external phase comprising pharmaceutically acceptable excipients and forming the mixture into an oral dosage form.

In still another aspect of the invention there is provided a method of preparing an oral dosage form comprising terbutaline sulphate and pharmaceutically acceptable excipients as described herein said method comprising the steps of:— i) admixing terbutaline sulphate with a pharmaceutically acceptable excipient to form an internal phase consisting of particles comprising terbutaline sulphate dispersed in a matrix of said excipient, and ii) mixing the particles of the internal phase with an external phase consisting of pharmaceutically acceptable excipients and forming the mixture into an oral dosage form.

These and other aspects and embodiments of the present invention are further described in the following detailed description.

The present invention is based on the surprising discovery that terbutaline sulphate degrades to its so-called "impurity B" when it is caused to interact with multiple excipients, such as when it is mixed together with two or more pharmaceutical excipients.

Excipients employed in the present invention include those typically employed in pharmaceutical preparations, such as diluents or fillers, binders, disintegrants, lubricants, flowing agents, release-controlling agents, surfactants, permeability regulating agents, chelating agents, colouring agents and the like, as more fully described below. Any excipients, such as those selected from the foregoing categories of excipients may be employed as the excipient, which together with terbutaline sulphate forms the internal phase.

The applicant observed that a stable dosage form could be obtained by taking the precaution to first mix terbutaline sulphate with a single excipient. By substantially coating or surrounding terbutaline sulphate by a single excipient in the formation of the internal phase, one can substantially avoid or at least reduce the contact of terbutaline sulphate with additional excipients, thereby preventing or reducing the likelihood of the multiple excipient interactions, which the applicant believes is the cause of the degradation problem.

Preferably, the internal phase comprises particles consisting essentially of a mixture of terbutaline sulphate and only a single excipient, although once the terbutaline sulphate is coated or surrounded in the manner described above, additional excipients can be added to the internal phase if desired. In a particular embodiment, the internal phase comprises further particles comprising one or more pharmaceutically acceptable excipients. Suitably, the internal phase consists essentially of terbutaline sulphate and two pharmaceutically acceptable excipients.

It is preferred that the excipient employed in the internal phase to coat or surround the terbutaline sulphate is a diluent or filler, as such excipients are typically employed in high amounts in an oral dosage form and can therefore be used in relatively high amounts in the internal phase to effect particularly good coverage of the terbutaline sulphate. A particularly preferred excipient is a diluent, preferably lactose monohydrate.

Preferably, the dosage form comprises 1 mg, 2.5 mg or 5 mg terbutaline sulphate. Suitably, the particles comprising a mixture of terbutaline sulphate and a pharmaceutically acceptable excipient comprise less than 25% terbutaline sulphate, preferably from about 3.7% to about 18.4% by weight of terbutaline sulphate.

Dosage forms of the present invention contain no more than 1% by weight of the impurity B, based on the amount of terbutaline sulphate contained in the dosage form, when subjected to storage under stress conditions more fully described hereinbelow.

The dosage forms useful in the present invention are adapted for oral administration and may take any form conventional in the art. For example, they may be presented in the form of tablets, capsules, multi-particulates in sachet or encapsulated form and the like.

Preferably the dosage form is in the form of a tablet. The tablet architecture may be selected having regard to the particular release profile that is sought. For example, the tablet may be monolithic, or of multi-layer construction, wherein the layers may be arranged in a sandwich-like fashion or concentrically. Alternatively, the dosage form may consist of a plurality of mini-tablets or multi-particulates that can be contained in a capsule or a sachet.

The dosage form of the present invention is preferably adapted to release terbutaline sulphate according to a modified release profile. Modified release dosage forms are defined by the USP as those whose drug release characteristics of time course and/or location are chosen to accomplish therapeutic or convenience objectives not offered by conventional immediate release dosage forms. More particularly, modified release dosage forms of the present invention release terbutaline sulphate over a period of several hours, e.g. 1 to 6 hours, post-administration or after immersion into a simulated gastro-intestinal medium.

In a particular embodiment of the present invention, the dosage form releases terbutaline sulphate with a delayed release profile. Still more particularly, a dosage form of the present invention is adapted to release terbutaline sulphate after a pre-determined lag time after ingestion, during which lag time no, or substantially no, terbutaline sulphate is released.

In a particular embodiment the dosage form releases the drug in a time-dependent manner, that is, drug release is independent of any changes in the physiological environment surrounding the dosage form, such as a change in pH or temperature or enzymatic or food conditions.

The lag time may be from 1 to 6 hours, still more particularly from 1 to 3 hours post ingestion, or post-immersion in a simulated gastric medium.

During the lag time no, or substantially no, terbutaline sulphate is released. By this is meant that the release of terbutaline sulphate from a dosage form described herein, during the lag time is in such small amounts that therapeutically effective blood plasma levels of terbutaline sulphate or the active agent thereof are not reached. In particular, in so far as any terbutaline sulphate is released, it is no more than about 10% of the total dose of terbutaline sulphate contained in a dosage form, still more particularly no more than about 5%, more particularly no more than about 1% or even less.

Following the expiry of the lag time, terbutaline sulphate begins to be released from the dosage form. It may be released according to any desired release profile. For example, it may be released rapidly or may be released slowly over a period of time (i.e. controlled or sustained release), or it may be dual released, that is rapid release, followed by a slow release, or slow release followed by a rapid release.

Examples of dosage forms adapted to release a drug after a lag time are known in the art. They have been proposed for use in treating morning conditions, diseases, or illnesses, such as arthritis, hypertension and asthma, the symptoms of which are generally acute in the morning as the patient awakens from sleep. These dosage forms are potentially very convenient for patients as they can be taken before bedtime and arrest symptoms that occur upon wakening. Without this type of pharmacological intervention patients would be required to either disturb their sleep to administer a conventional dosage form prior to their normal wakening time, or remain un-medicated and suffer the morning symptoms.

Nocturnal hypoglycaemia is not such a morning condition, disease or illness. It is a condition the onset of which symptoms occurs as a patient sleeps. It is a condition that is associated with substantial morbidity and mortality and it is important to recognise, diagnose and treat properly. In certain circumstances, if the symptoms do not cause the patient to wake, the patient remains unaware of the developing symptoms and therefore uncontrolled. In such cases, the treatment's effectiveness, or lack thereof, can only be determined once the patient awakens from sleep when it is too late to arrest the symptoms and in severe cases emergency treatment may be called for to treat acute symptoms. Nocturnal hypoglycemia in insulin treated diabetes patients is a life threatening event.

Dosage forms of the present invention may be coated with a non-functional coating or coatings, that is, a coating that does not influence the lag time or release rate of the dosage form. Such coatings include those employed to achieve an aesthetic effect (e.g. an attractive colour or pleasant taste) or information effect, e.g. a coating may be coloured to act as a visual cue to enable a patient to identify a medicament. Coatings may also be over-written with information relating to the dosage form, or they may elicit a handling effect, e.g. a smooth coating for ease of swallowing, or a stability effect, e.g. a moisture or light barrier during storage.

Excipients are employed in the oral dosage form to optimise the bulk properties of the dosage form and to affect the desired release profile. Categories of excipients include diluents or fillers, binders, disintegrants, lubricants, flowing agents, release-controlling agents, surfactants, permeability regulating agents, chelating agents, colouring agents and the like.

Diluents or fillers are employed to add bulk to a formulation to enable formulations of a desired size to be prepared; binders promote the adhesion of the particles of a formulation to maintain the integrity of the dosage form during its manufacture, handling, storage or subsequent use; disintegrants or disintegrating agents, promote the break-up of the dosage form after ingestion to make the ingredients more readily available; lubricants or flowing agents, enhance the flow of the dosage form ingredients during manufacturing operations, for example they prevent sticking of a formulation to tablet-making machinery; release-controlling agents and permeability regulating agents can be employed to affect the way a drug is released from a dosage form and other miscellaneous adjuvants can be employed such as colourants and flavourants.

Suitable diluents include pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel grades, PH101 PH102, PH112, PH113, PH200, PH300, PH301, HFE 102 (co-processed with mannitol), DG (coprocessed with dicalcium phosphate), CE 15 (co-processed with guar gum); lactose such as lactose monohydrate, lactose anhydrous, and Pharmatose DCL 21; dibasic calcium phosphate such as Emcompress or Calipharm; mannitol; starch; sorbitol; fructose; sucrose; and glucose. Diluents are carefully selected to match the specific requirements of the formulation. The diluent is preferably used in an amount of 10% to 90% by weight, more particularly 50% by weight, of the dosage form.

Suitable lubricants and glidants including agents that act on the flowability and compressibility of the powder to be tabletted are, for example, colloidal silicon dioxide such as Aerosil 200, Cab O Sil; talc; stearic acid, magnesium stearate, calcium stearate, sodium stearyl fumarate, polyethylene glycol and sodium lauryl sulphate. The lubricant is preferably used in an amount of 0.5 to 2% by weight, in particular 1% by weight, of the dosage form.

Suitable binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; waxes, alginic acids and salts thereof; HPC; HPMC; methylcellulose; maltodextrin and dextrin; povidone; gums; starch and modified starches. The binder preferably may be used in an amount of 2 to 10% by weight, more particularly 5% by weight, of the dosage form.

Suitable disintegrants include sodium starch glycolate, such as Explotab, crospovidone such as Kollidon CL, polyplasdone XL, sodium carboxymethylcellulose, sodium croscarmellose such as AcDiSol, and starch. The disintegrant preferably may be used in an amount of 2 to 10% by weight, more particularly 5% by weight, of the dosage form.

If an immediate burst of terbutaline sulphate is required upon expiry of the lag time, the dosage form may comprise a surface-active agent such as sodium lauryl sulfate, sodium monoglycerate, sorbitan monooleate, polyoxyethylene sorbitan mono-oleate, glyceryl monostearate, glyceryl mono-oleate, glyceryl monobutyrate, any one of the Pluronic line of surface-active polymers, or any other suitable material with surface active properties or any combination of the above.

Surface active materials may be present in the dosage form in amounts of 0.1 to 10% by weight.

The total excipients employed may be present in the dosage form in amounts of 10 to 99% by weight.

Additional examples of pharmaceutically acceptable carriers and excipients that can be used to formulate oral dosage forms are described in the Handbook of Pharmaceutical Excipients, American Pharmaceutical Association (APhA).

The term controlled release as it relates to a dosage form of the present invention refers to a the dosage form, or a part thereof that is adapted to release terbutaline sulphate within a certain time to accomplish a therapeutic objective not possible using a conventional immediate release dosage form.

The controlled release phase may contain any of the aforementioned excipients described above in the amounts already mentioned. However, in addition the controlled release phase should contain a release rate controlling agent or agents.

The term "release rate controlling agent" includes any agent or agents that alone or in combination, optionally together with other excipients, controls the rate of release of terbutaline sulphate in terms of duration, in order to give a therapeutic effect not possible with a conventional immediate release formulation, and includes hydrophilic polymers, hydrophobic polymers or mixtures thereof, or copolymers thereof, or mixtures of these polymers and copolymers.

The release controlling agent may be in a matrix in which terbutaline sulphate is dissolved or dispersed. Alternatively, the release controlling agent may be in a layer or coating surrounding a matrix containing terbutaline sulphate. Still further, it may be employed in a matrix and a coating.

By selecting appropriate matrix and/or coating materials one is able not only to accurately control the lag time, one is also able to ensure that all, or substantially all, of the terbutaline sulphate upon expiry of the lag time is released at a desired rate to achieve a desired therapeutic effect.

Dosage forms of the present invention, after expiry of the lag time, may vary in release rate characteristics from immediate release to controlled release, or a mixed profile of immediate release and controlled release. Release may be continuous or pulsatile.

Examples of release-rate controlling agents to be used in this invention include hydroxyalkylcellulose, such as hydroxypropylcellulose and hydroxypropylmethylcellulose; poly(ethylene)oxide; alkylcellulose such as ethycellulose and methylcellulose; carboxymethylcellulose; hydrophilic cellulose derivatives; polyethylene glycol; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable polymers include polymers or copolymers derived from acrylic or methacrylic acid esters, copolymers of acrylic and methacrylic acid esters, zein, waxes, shellac, semi synthetic glycerides and hydrogenated vegetable oils.

The release-rate-controlling agent may include a hydroxypropyl methylcellulose (HPMC), a hydroxypropyl cellulose (HPC), a poly(ethylene oxide), an ethylcellulose or a combination thereof, in particular present in an amount of 5 to 90% based on the weight of the dosage form.

Preferred types of HPMC for use in accordance with the invention are those sold under the trademark Methocel (Dow Chemical Co.). Suitable Methocels include the K grades such as Methocel K 15M, Methocel K 100M, Methocel K 100LV and Methocel K 4M. Other suitable Methocels include the E, F and J grades.

As HPCs there can be employed those sold under the trademark Klucel (Hercules, Inc.) or equivalents. Suitable Klucels include Klucel LF, Klucel JF, Klucel GF, Klucel MF and Klucel HF.

As poly(ethylene oxide)s there may be mentioned those sold under the trademark Sentry Polyox (Union Carbide Corp.) or equivalents. Suitable Polyoxs include the Polyox WSR grades such as Polyox WSR Coagulant, Polyox WSR-301, Polyox WSR-303, Polyox WSR N-12K, Polyox WSR N-60K, Polyox WSR-1105, Polyox WSR-205 and Polyox WSR N-3000.

As ethylcelluloses for use in accordance with the invention there can be mentioned those sold under the trademark Ethocel (Dow Chemical Co.) or equivalents.

The hydroxypropylmethylcelluloses preferably have a viscosity (2 wt % solution at 20 degree. C.) of about 5 to 100,000 mPa*s, preferably 4,000 to 100,000 mPa*s. Especially suitable are Methocel K types or their equivalents. The hydroxypropylmethylcelluloses used according to the invention preferably have a number average molecular weight of about 80,000 to 1,150,000, more preferably 80,000 to 600,000.

Poly (ethylene oxide) preferably has number average molecular weights of about 100,000 to 7,000,000, more preferably 900,000 to 7,000,000. Especially suitable is Polyox WSR Coagulant, which has a molecular weight of 5,000,000. The ethylcelluloses used according to the invention preferably have a viscosity of about 3 to 10 mPa*s, more preferably 7 to 100 mPa*s.

Additional example of materials or excipients that may form part of a controlled release matrix are contained in Remingtons Pharmaceutical Sciences, 18th ed. Mack Publishing Co., Easton, Pa., 1990, p. 1684-1685), which is incorporated herein in its entirety for this purpose.

In a dosage form according to the present invention, the internal phase and external phase may be in the form of a core containing terbutaline sulphate, which core is surrounded by a coating that may be applied by press-coating. The dose of terbutaline sulphate may be a low dose, e.g. 1 to 5 mg, more particularly 1, 2, 2.5, 3, 4 or 5 mg. The coating acts as a barrier layer that enables terbutaline sulphate to be released after a lag time, which may be about 1 to 3 hours. Thereafter, terbutaline sulphate may be released according to a desired release profile, e.g. rapid release in which 100% is released within 60 minutes.

The core may contain any of those excipients mentioned above, but in particular it may contain a diluent such as lactose monohydrate, dibasic calcium phosphate dihydrate, xylitol or microcrystalline cellulose; a binder such as povidone; a surfactant such as sodium lauryl sulphate; a disintegrant such as croscarmellose sodium, pre-gelatinised starch, or crospovidone; a flow agent such as colloidal silicon dioxide; a lubricant such as magnesium stearate; a permeability regulator such as glyceryl behenate; a colouring agent such as ferric oxide; a chelating agent such as edetic acid; a solubiliser such as poloxamer; and an antioxidant such as ascorbic acid, citric acid, malic acid, tartaric acid, sodium metabisulphite, meglumine, tromethamine or butylhydroxytoluene.

Particularly preferred core and coating excipients are described in the examples set forth below.

In order to facilitate the preparation of dosage forms described herein there is provided, in a further aspect of the present invention, a process for the preparation of a dosage form useful in the present invention as described above.

Both the mixing step i) and the mixing step ii) described above, independently of each other, may be carried out using any suitable technique known in the art. For example, in each step the mixing may be carried out by dry blending, dry granulation (slugging and roller compaction) or wet granulation.

Examples of wet granulation techniques include fluid bed granulation, tumbling fluidized bed granulation, centrifugal granulation, stirring granulation, spray granulation, and extrusion granulation.

In the present invention, high shear wet granulation can be employed to granulate terbutaline sulphate and the excipient or excipients, e.g. lactose monohydrate, in the internal phase. The granulation may be carried out by a conventional method, for example, as follows: In a typical procedure, terbutaline sulphate and the excipients are sieved and blended. Granulating fluid, typically water (although organic solvents such as ethanol, isopropyl alcohol, acetone or methylene chloride can be used) is then added to the blend and the mixture is homogenized to form a granulate, which is then sprayed dried or dried on a fluid bed drier to obtain a granulate with requisite residual moisture. Preferably the residual moisture content is from about 0.4 to 2.0% by weight. The granulate is then sized by passing it through screens of desired aperture. At this stage, other excipients can be sized and added to the granulate, e.g. by a process of dry blending, to form a core composition that is suitable for compression.

Therefore, in a particular embodiment of the present invention there is provided a method of forming an oral dosage form comprising terbutaline sulphate and pharmaceutically acceptable excipients said method comprising the steps of:— i) granulating terbutaline sulphate with pharmaceutically acceptable excipients, preferably a single pharmaceutically acceptable excipient, to form a granulate comprising terbutaline sulphate dispersed in a matrix of said excipient, and ii) mixing the granulate formed in step i) with other pharmaceutically acceptable excipients and forming the mixture into an oral dosage form.

The mixture of terbutaline sulphate and excipients can be formed into a dosage form, e.g. a tablet, by compression methods. Compression methods involve the application of high pressure to powders or granulates utilizing steel, e.g. stainless steel, punches and dies. In this manner a wide variety of shapes, sizes and surface markings can be formed depending on the size and design of the punches and dies employed. On an industrial scale they may be produced using rotary presses, e.g. a Manesty press, Liverpool, United Kingdom or a Korsch and Killian press, Berlin, Germany. Presses generally operate at pressures of about 1000 to about 5000 kg/cm$^2$.

Should coating of the dosage form be desired, this can be achieved using known coating techniques such as press coating, spray coating, pan coating or air suspension coating techniques generally known in the art. All of the techniques discussed above are described in detail in Ansel's Pharmaceutical Dosage Forms and Drug Delivery Systems, Chapter 7, Seventh Edition, 1999 (Lippincott Williams & Wilkins), which is herein incorporated by reference for this purpose.

A particularly preferred dosage form of the present invention is a press-coated tablet. A press-coated tablet comprises a tablet core formed by compression of the mixture of excipients and terbutaline sulphate described above, which is over-coated with a coating formed around the core by compression.

The core architecture may be in any desired form. For example, the core may be monolithic or multi-layered, and the layers may be arranged in a sandwich-like fashion or concentrically.

The core may be adapted to release terbutaline sulphate with immediate release when it comes into contact with a physiological medium. Alternatively, the core may be adapted to release terbutaline sulphate with controlled or sustained release. Still further, the core may be adapted to release in a sequential manner first fast, then slow or slow then fast. Still further, release may be pulsatile. The skilled person will appreciate that all manner of release profiles can be achieved having regard to the composition of the core as well as the properties of the coating.

Preferably, the coating comprises one or more water insoluble or poorly soluble hydrophobic excipients. Preferably these excipients are selected from fatty acids or their esters or salts; long chain fatty alcohols; polyoxyethylene alkyl ethers; polyoxyethylene stearates; sugar esters; lauroyl macrogol-32 glyceryl, stearoyl macrogol-32 glyceryl, and the like.

Other excipients that provide a hydrophobic quality to coatings may be selected from any waxy substance known for use as tablet excipients. Said waxy substances may have a HLB value of less than 5, and more preferably about 2. Suitable waxy substances include carnauba wax, paraffin, microcrystalline wax, beeswax, cetyl ester wax and the like; or non-fatty hydrophobic substances such as calcium phosphate salts, e.g. dibasic calcium phosphate.

Coatings comprising the aforementioned materials provide for a lag time by acting as a barrier to physiological media thereby delaying said media reaching the tablet core. Once the medium crosses the coating and enters the core, it may cause the core matrix to hydrate and expand, for example by swelling, gelling or effervescing. The mechanical pressure exerted on the coating by the action of the core causes it to rupture, exposing the core to the physiological medium and permitting release of terbutaline sulphate from the core according to the desired release profile.

Preferred components in the coating are as follows, with generally suitable percentage amounts expressed as percentage weight of the coating.

Polyvinylpyrrolidone (Povidone) is preferably present in amounts of about 1 to 25% by weight or the coating, more particularly 4 to 12%, e.g. 6 to 8%.

Glyceryl behenate is an ester of glycerol and behenic acid (a C22 fatty acid). Glyceryl behenate may be present as its mono-, di-, or tri-ester form, or a mixture thereof. Preferably it has an HLB value of less than 5, more preferably approximately 2. It may be present in amounts of about 5 to 85% by weight of the coating, more particularly from 10 to 70% by weight, and in certain preferred embodiments from 30 to 55%.

Calcium phosphate salt may be the dibasic calcium phosphate dihydrate and may be present in an amount of about 10 to 90% by weight of the coating, preferably 20 to 80%, e.g. 40 to 75%.

The coating may contain other common tablet excipients such as fillers, binders and the like, commonly used in forming solid oral dosage forms.

The coating thickness surrounding the core will influence the lag time, and can also affect the rate of drug release thereafter depending on the nature of the coating materials.

Press-coating provides a particularly effective means of controlling coating thickness, and therefore controlling lag time.

Press-coating is particularly advantageous as one can control coat weight, diameter of die and size of core to achieve a precisely defined minimum coating thickness at selected points on the dosage form. The time taken for a physiological medium to cross the coating at the coating's narrowest section will determine the time it takes for the core to begin to hydrate and break the coating.

The thickness of the coating in the plane orthogonal to the direction of compression of the punch can be precisely controlled. Here the physiological medium can cross the coating and eventually in this plane the coating will rupture. The lag time can determined by the thickness and density of the coating in this plane.

Preferably, the thickness of the coating in this plane should be about 0.5 to 5 mm, more particularly 1 to 3 mm in order to achieve a lag time of approximately 1 to 3 hours.

Press-coated tablets can be conveniently prepared by placing a portion of a powdered coating material in a die and tamping the powder into a compact form using a punch. A tablet core, preformed by compression, is then deposited onto the compacted coating material before the remainder of the coating material is introduced into the die to cover the core, and compression forces are applied to form the coated dosage form. To ensure that the core is placed on the tamped coating material and to ensure it is correctly positioned in order that the coating thickness will be uniform about the afore-mentioned orthogonal plane, it is preferable to employ means for positioning the core in relation to the coating material in a die. Typically such means may be provided by a pin punch or a double punch. A pin punch is a punch that has a convex surface that contacts the coating material to leave a small depression or hollow in the tamped coating material. Thus, when the core is placed into the die on the tamped material, it sits in the depression or hollow and in this way, it is correctly positioned within the tablet in its completed press-coated form.

When selecting coating materials, it is preferred not to employ materials that are swellable or gellable. Typical of such materials are cellulose ethers or cellulosic derivatives such as hydroxyalkyl celluloses, e.g. hydroxypropylmethyl cellulose, or carboxyalkylcelluloses and the like. Such materials tend to form gels which exert a release-controlling effect by forming an erodible barrier through which drug substance may diffuse. Such materials tend to give unreliable lag times and should be avoided in amounts that exert a release-controlling effect. Their release-controlling properties are usually evident when they are employed in amounts of about 10% or greater. Preferably therefore, if any of the aforementioned materials are employed as coating materials they should only be used in small amounts, e.g. less than 10%, more particularly less than 5%, still more particularly less than 1%.

Press-coated dosage forms according to the invention may be over-coated with a pharmaceutically acceptable film-coating, for aesthetic purposes (e.g. including a colourant), for stability purposes (e.g., coated with a moisture barrier), for taste-masking purposes, or for the purpose of protecting unstable drug substances from aggressive media, e.g. enteric coatings.

The hardness of the dosage form is preferably at least 40 Newtons, e.g. 40 to 80 Newtons, and more particularly 60 to 75 Newtons. Hardness may be measured according to a process described in The European Pharmacopoeia 4, 2.9.8 at page 201.

Dosage forms having an hardness within this range are mechanically robust to withstand forces generated in the stomach, particularly in the presence of food. Furthermore, the dosage forms are sufficiently porous to permit physiological media to cross the coating and interact with the core at an appropriate rate to achieve the desired lag times referred to herein.

Press-coated dosage forms may be formed on conventional press coating equipment. Typically such equipment is composed of a series of dies arranged on a rotating platform (turntable). Each is removably mounted in the platform such that differently sized die may be employed as appropriate. Each die is hollow to receive a lower punch. The punch is positioned, within the die such that the upper surface of the punch and the inner surface of the die define a volume for receiving a precise amount coating material. Once loaded, the turntable is rotated until the die is positioned under an upper punch. The upper punch is then urged down onto the coating material under a defined compression force and the coating material is pre-compressed or tamped between the upper and lower punch. A preformed core is then fed into a die to rest on the tamped coating. Conventional press coating apparatus may be equipped with centering devices that enable cores to be positioned both vertically and radially. This might be achieved by a tamping process, whereby an initial amount of coating material is placed in a die and is tamped with a shaped punch, such as a pin punch, that leaves an indentation in the coating material in which to receive a core. Thereafter, in a second filling operation, a precise amount of coating material is fed into the die to cover the core, and an upper punch compresses the coating material with a defined compaction force to form press-coated dosage forms. The compression force applied during the tamping process is relatively light and is just sufficient to provide a bed of coating material to receive the core and to prevent movement of the coating material as a result of centrifugal force. Subsequent compression to form the dosage form may be adjusted to give a requisite hardness.

Preferably, this compression force is 400 kg, although this may be adjusted by +/−30% in order to give tablets having desirable physical properties.

The amount of coating material fed into a die can be precisely defined having regard to the density of the coating material, as can the dimension of the die to ensure after compression that the dosage form is formed with the required coating thickness. Should it be necessary to change the thickness of the coating, die of appropriate internal dimensions may be placed in the rotating platform, and the amount of coating material fed into the die may be adjusted accordingly.

Suitable rotary tablet machines having high process speeds are known in the art and need no further discussion here.

Cores may likewise be formed using a conventional rotary tablet machine. Cores are preferably compressed under compression forces sufficient to provide a hardness of about 60 Newtons at least, e.g. 50 to 70 Newtons. Cores having hardness in this range give desired release characteristics. If desired, the cores can be formed at the same time as the press coated tablets are produced. In such case, one might employ a Manesty Dry Cota. This press consists of two side-by-side and inter-connected presses where the core is made on one press before being mechanically transferred to the other press for compression coating. Such equipment and techniques for making dosage forms using such equipment are known in the art and no more needs to be said about this here.

Dosage forms of the present invention are useful in treating nocturnal hypoglycaemia. More particularly, they are useful in the treatment of nocturnal hypoglycaemia and can also overcome the reported side effects to produce a more pronounced normoglycaemic effect during the night and avoiding morning hyperglycaemia. The benefits of such a treatment are clearly useful to treat nocturnal hypoglycaemia whatever its cause, but is particularly useful for insulin treated type I and type II diabetes patients where hypoglycaemia has been a recurring problem and presents severe safety risks. It also is useful for a larger population of diabetics treated with insulin to allow for more aggressive blood glucose control without increasing the risk of hypoglycaemia. More aggressive glucose control therapy usually includes setting specific goals for maintaining blood sugar levels within a certain range before and after meals and attempting to achieve a quarterly haemoglobin Ale (test measuring average glucose over a three-month period) of less than about 7%. Glucose control therapy requires frequent injections of insulin, close monitoring of dietary habits, regular use of exercise and frequent blood sugar tests.

The present invention provides dosage forms, regimens and methods, which provide for the treatment of nocturnal hypoglycaemia in patients, more particularly, without eliciting, or at least minimizing, adverse effects such as hyperglycaemia upon wakening in the morning and/or worsening glucose control.

In another aspect of the present invention there is provided a method of treating nocturnal hypoglycaemia and simultaneously preventing or reducing the incidence of hyperglycaemia in a subject upon wakening, with a dosage form as defined herein. More particularly with a dosage form as defined herein that is adapted for modified release. Still more particularly, with a dosage form as defined herein that is adapted to release terbutaline sulphate after a lag time as described above.

In another aspect of the invention there is provided a method of treating nocturnal hypoglycaemia with an oral dosage form as defined herein, wherein said oral dosage form, when tested in a group of human subjects provides a time ($T_{max}$) to mean peak plasma concentration ($C_{max}$) between 1 hour and 6 hours of administration of said dosage form, more particularly between 2 to 3 hours of administration of said dosage form.

In another aspect of the invention there is provided a method of treatment of nocturnal hypoglycaemia with an oral dosage form defined herein, which dosage form, when tested in an in-vitro simulated intestinal fluid, releases terbutaline sulphate over a period of time defined by an in-vitro dissolution profile wherein not more than 10% of the dose of terbutaline sulphate is released after 1 or 2 hours; at least 80% released after 6 hours, and at least 100% released after 10 hours.

The sleep patterns of children and adults can differ substantially. Children generally go to bed earlier than adults and the duration of their sleep tends to be longer than adults. Accordingly, the release profiles described above may be tailored for different patient populations.

In a particular embodiment, particularly suitable for children, there is provided a method of treatment of nocturnal hypoglycaemia with a dosage form defined herein, wherein the dosage form, when tested in an in-vitro simulated intestinal fluid, releases terbutaline sulphate over a period of time defined by an in-vitro dissolution profile wherein not more than 10% of the dose of terbutaline sulphate is released after 1 or 2 hours; at least 50% released after 4 hrs, and at least 80% released after 8 hours.

In another embodiment there is provided a method of treatment of nocturnal hypoglycaemia with a dosage form as herein defined, wherein the dosage form, when tested in an in-vitro simulated intestinal fluid, releases terbutaline sulphate over a period of time defined by an in-vitro dissolution profile wherein not more than 10% of the dose of terbutaline sulphate is released after 1 or 2 hours, at least 80% released after 4 hrs, and at least 100% released after 6 hours.

The simulated intestinal fluid (SIF) is an aqueous phosphate buffer solution at a pH of 6.8. A suitable simulated fluid for this purpose consists of 68.05 g of potassium dihydrogen phosphate and 8.96 g of sodium hydroxide dissolved in 10 liters of deionized water. As an alternative to SIF one may employ purified water as the dissolution medium. The in-vitro test may be carried out in accordance with the USP apparatus II with paddle rotation at 100 rpm.

The USP monograph for terbutaline sulphate tablets recommends USP apparatus I. However, USP Apparatus II is the preferred method for the purpose of the present invention as the dosage form is intended to be released in the lower GI tract and will be subjected to relatively high mechanical stress during transit prior to release. USP II apparatus at 100 rpm creates particularly high turbulent forces that better reflect the mechanical forces on the oral dosage form in-vivo. Stationary baskets could be used to maintain the dosage form in the high turbulence zone located under the paddle.

Procedures for carrying out in-vitro dissolution tests are well known in the art. Typically a dissolution apparatus may be set by programming the temperature, rotation and run time at 37 degrees centigrade, 100 rpm and 12 hours. 900 ml of dissolution medium is placed in each of six vessels of the dissolution apparatus. The apparatus is assembled and the dissolution medium is equilibrated to 37 degrees and the thermometer is removed. One unit dosage form is placed in each of the six vessels. Rotation of the paddle is started at the speed of 100 rpm for 12 hours. Aliquots (each of 6 ml) are withdrawn, and successively replaced with equal volumes of fresh dissolution medium, at the desired interval periods from each of the six vessels.

The amount of dissolved terbutaline sulphate can be determined conventionally by HPLC. Detection can be by UV absorption at a wavelength of 235 nm. Quantification can be effected by comparison of HPLC peak height (or area) with the peak height (or area) taken from a standard plot of concentration vs. peak height (or area) for standards of known concentration.

The test preparations are separately injected into the chromatograph after filtering through 0.45 micron membrane filter. Chromatograms are recorded and the peak responses of the test peak are compared in terms of area with a standard. The quantity of terbutaline sulphate released in percent (%) can then be calculated.

The pharmacokinetic parameters $T_{max}$, $C_{max}$ and AUC are terms well known in the art. $T_{max}$, $C_{max}$ and AUC can be obtained by plotting blood plasma concentrations of a drug (Y-axis) against time (X-axis). $C_{max}$ is the observed maximum of this plot and $T_{max}$ is the time to the observed $C_{max}$. $AUC_t$ corresponds to the area under the curve up to certain sampling points (or extrapolated in some cases) and reflects the bioavailability of the drug for a given route of administration. These values are typically measured as mean values.

The term "mean" as used herein in relation to these pharmacokinetic parameters represents the arithmetic mean value measure across a patient population (usually at least 10 patients).

In another aspect of the invention there is provided an oral dosage form as herein defined, which when tested in a group of human subjects, achieves for a dose of 5 mg terbutaline sulphate a mean peak plasma concentration (Cmax) of terbutaline of about 2.5 to 5 ng/ml; and for a dose of 2.5 mg terbutaline sulphate a mean peak plasma concentration of about 1.0 and 2.5 ng/ml.

In another aspect of the invention there is provided a treatment regimen for treating nocturnal hypoglycaemia using a dosage form as defined herein, wherein the dosage form is administered according to a schedule wherein 0.1 to 10 mg, more particularly 1.0 mg, 2 mg, 2.5 mg, 3 mg, 4 mg or 5 mg of terbutaline sulphate is administered to a subject once a day before bedtime.

By "bedtime" as this term relates to the dosing schedule described above, is meant a period immediately before a subject retires to bed for sleep. This period may differ from subject to subject, and substantially when comparing children's sleeping habits with adults. More particularly, bedtime is between about 7 pm to midnight, still more particularly about 7 to 9 pm for children and between 10 pm and midnight for adults.

In another aspect of the invention there is provided a treatment regimen for treating nocturnal hypoglycaemia using a dosage form as defined herein, wherein the dosage form is administered according to a schedule whereby 0.1 to 10 mg dose of terbutaline sulphate once a day before bedtime and taken either simultaneously with food or after food.

In a particular embodiment of the present invention the food is a carbohydrate-containing beverage or food. A standard cornstarch bar provides about 39 g of carbohydrates, 4 g of fat and the same of proteins.

The methods and regimens referred to herein are useful in the treatment of nocturnal hypoglycaemia, however the condition is caused and in any patient population. In particular, the methods and regimens described herein are useful in the treatment of nocturnal hypoglycaemia in patients being treated for type I or type II diabetes. Still further, reactive hypoglycaemia (hypoglycaemia a few hours after a meal) fasting hypoglyacaemia (hypoglycaemia on an empty stomach), hypoglycaemia caused by oral diabetes drugs, beta-blockers or other drug interactions, hypoglycaemia caused by insulin-secreting pancreatic tumour, alcohol-induced hypoglycaemia, alimentary hypoglycaemia (rapid jejunal emptying with exaggerated insulin response), hypoglycaemia after gastrectomy, tumour hypoglycaemia, hormonal hypoglycaemia (e.g. acquired adrenal insufficiency or acquired hypopituitarism), immunopathologic hypoglycaemia, or hypoglycaemia caused by congenital enzyme deficiencies such as galactosemia and hereditary fructose intolerance.

The methods and regimens described herein are useful in the treatment of nocturnal hypoglycaemia, a contributory cause of which is the use of another medication, whether taken to treat diabetes or otherwise. Examples of such medication include but are not limited to insulin or other antidiabetic medications including oral hyperglycaemic agents, ethanol, Beta blockers, e.g. propranolol, salicylates, Acetaminophen, Acetazolamide, Aluminium hydroxide, Chloroquine, Chlorpromazine, Cimetidine, Ranitidine, Diphenhydramine, Propoxyphene, Disopyramide, Doxepin, Isoxsuprine, Insulin-like growth factor 1, Lidocaine, Lithium, Pentamidine, Propranolol, nadolol, labetalol, metoprolol, Orphenadrine, Oxytetracycline, Quinine, quinidine, Perhexiline, Ritodrine, Haloperidol, Chelating agents, Colchicine, Para amino benzoic acid, para-amino salicylic acid, Cholestyramine added during glucocorticoid therapy (reduces absorption), Drugs which lower glucose in diabetics mentioned above, Enalapril and captopril, Coumarin, Phenylbutazone, Antihistamines, Sulfa antibiotics, Monoamine oxidase inhibitors, Azapropazone, buformin, carbutamide, cibenzoline, cycloheptolamide, glibornuride, gliclazide, mebanazine, metahexamide, perhexiline, sulphadimidine and sulphaphenazole.

For the purpose of the present invention, such medications described above are considered to be a "first medication".

In another aspect of the present invention there is provided a method or regimen for the treatment of nocturnal hypoglycaemia in a patient in need thereof comprising the step of (a) determining if said patient is undergoing treatment with one or more first medications and (b) administering a dosage form as defined herein to said patient based on said patient's treatment with said one or more first medications.

The first medication could be a medication used to treat diabetes, in which case, terbutaline sulphate may be used as an adjunctive therapy to this first medication, or the first medication could be administered to treat a condition other than diabetes.

In yet another aspect of the invention said methods described hereinabove employ a dosage form in a kit comprising packaging or labelling advising subjects regarding one or more first medication, or advising on dosing relative to the use of said one or more first medication.

There now follows a series of examples that serve to illustrate the invention.

EXAMPLE 1

A press coated tablet according to the invention has the following composition set forth in the table below:—

| Content | % | mg/tablet |
|---|---|---|
| Blend 1 (Core) | | |
| Internal phase | | |
| Internal Phase 1 | | |
| Terbutaline sulphate | 1.68 | 1.00 |
| Lactose pulvis, H$_2$O | 43.66 | 26.20 |
| Internal Phase 2 | | |
| Lactose pulvis, H$_2$O | 43.66 | 26.20 |
| Ac-Di-Sol | 5.00 | 3.00 |
| External Phase | | |
| Ac-Di-Sol | 5.00 | 3.00 |
| Aerosil 200 | 0.50 | 0.30 |
| Magnesium stearate | 0.50 | 0.30 |
| Total, layer | 100.00 | 60.00 |
| Blend 2 (Mantle) | | |
| Internal Phase | | |
| Dibasic calcium phosphate, 2H$_2$O | 38.876 | 207.60 |
| Compritol 888 ATO | 21.101 | 112.68 |
| Xylitol 300 | 20.000 | 106.80 |
| Avicel PH101 | 10.000 | 53.40 |
| SLS | 2.247 | 12.00 |
| Plasdone K29-32 | 6.530 | 34.87 |
| Sicovit Yellow 10 E 172 | 0.079 | 0.42 |
| External Phase | | |
| Aerosil 200 | 0.389 | 2.08 |
| Magnesium stearate | 0.778 | 4.15 |
| Total, layer | 100.000 | 534.00 |
| Final product, mg | — | 594.00 |

Preparation of Blend 1:

Blend 1 has 2 internal phases. The first one corresponds to terbutaline sulphate dry mixed with a fraction of the lactose monohydrate. Thereafter the blend is wet granulated in a high shear mixer prior drying in a fluid bed dryer. The dry granules formed are then sized in an oscillatory mill.

The second internal phase corresponds to AcDiSol dry mixed with a fraction of the lactose monohydrate. Thereafter the blend is wet granulated in a high shear mixer prior drying in a fluid bed dryer. The dry granules are then sized in an oscillatory mill.

Thereafter internal phase 1 and 2 are blended together in a diffusion blender prior addition of glidants and lubricant (external phase) to form blend 1 ready to be compressed to give active cores of the press coated tablet.

Blend 2 corresponds to the mantle (coating) of the press coated tablet. All ingredients of the internal phase are dry mixed together. Thereafter the blend is wet granulated in a high shear mixer prior drying in a fluid bed dryer. The dry granules are then sized in an oscillatory mill.

External phase is then added to the granule in a diffusion blender to form the mantel blend ready to be pressed onto the active cores already prepared with blend 1.

Note, whereas this example refers to a 1 mg dose terbutaline sulphate formulation, higher doses can be formed with the excipients described in the table, duly modified such that as higher amounts of terbutaline sulphate are employed, the amount of lactose is reduced by a corresponding amount such that the total weight of terbutaline sulphate and lactose remains constant.

EXAMPLE 2

Figure 1:
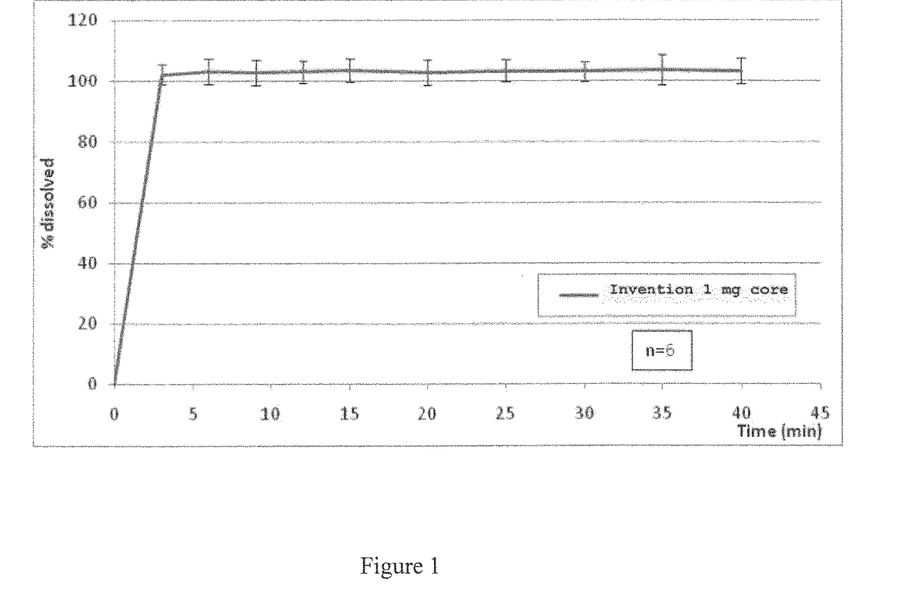
FIG. 1: Mean dissolution profiles of active core obtained with Blend 1 of Example 1.

Mean (N=6) dissolution profiles of active core obtained with blend 1 of Example 1 are presented in FIG. 1. The dissolution test is conducted in USP apparatus II with 100 rpm paddle speed and stationary baskets in acetate buffer pH 5.5. Collected fractions are analysed by HPLC method.

EXAMPLE 3

Figure 2:
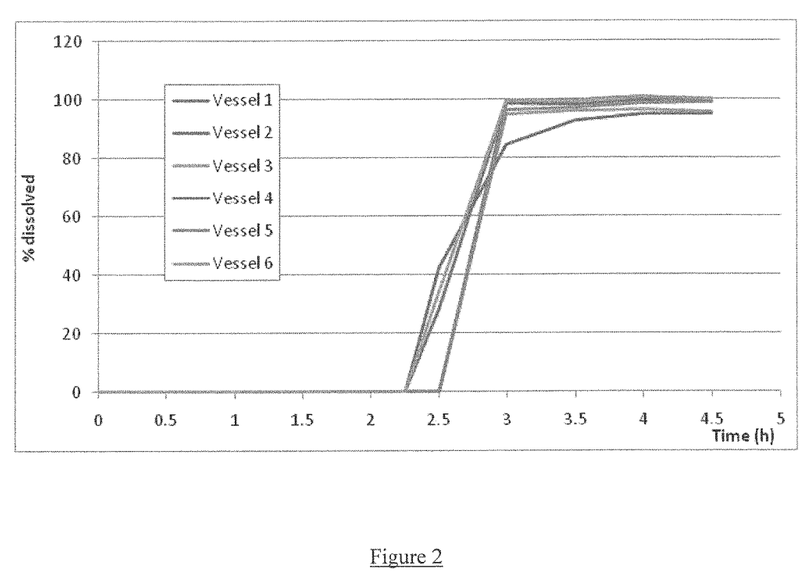
FIG. 2: Individual dissolution profiles of press coated tablets prepared according to Example 1.

Individual dissolution profiles of press coated tablets prepared according to Example 1 are presented in FIG. 2. The dissolution test is conducted in USP apparatus II with stationary baskets at 100 rpm paddle speed in 500 ml of water. Collected fractions are analysed by HPLC method.

EXAMPLE 4

Impurity B levels at $T_0$ for formulations prepared according to Example 1 at 1 mg, 2.5 mg and 5 mg have been tested and are compared in Table 1 with results obtained with a tablet formulation prepared by mixing all of the core excipients and terbutaline sulphate in a one step process approach (reference).

$T_0$ represents the initial testing of the formulations just after end of manufacturing Ti are designating the stability time points in months following storage of tablets at 40° C./75% RH. Impurity B levels for the invention formulations after 18 and 24 months storage are below the level reached after 6 months for the corresponding reference formulation.

The stability test is carried out on tablets packed in 75 ml white HDPE bottles with screw cap-closure and desiccant inside the cap (90 tablets per bottle) and then stored in climatic chambers.

TABLE 1

| Formulation | Strength | Impurity B level | | | | | |
|---|---|---|---|---|---|---|---|
| | | T0 | T1 m | T3 m | T6 m | T18 m | T24 m |
| Reference | 1 mg | 0.23% | 0.50% | 1.14% | 1.99% | np | np |
| Invention | | <LOD | 0.16% | 0.34% | 0.49% | 0.61% | 0.61% |
| Reference | 2.5 mg | <0.10% | 0.21% | 0.45% | 0.78% | np | np |
| Invention | | <LOD | <0.10% | 0.16% | 0.20% | 0.23% | np |
| Reference | 5 mg | <LOD | 0.10% | 0.38% | 0.38% | np | np |
| Invention | | <LOD | <LOD | <0.10% | 0.12% | 0.13% | np |

LOD: limit of detection (0.05%)
LOQ: limit of quantification (0.10%)
np: not performed
Specifications for release and stability ≤1.0%

EXAMPLE 5

Figure 3:
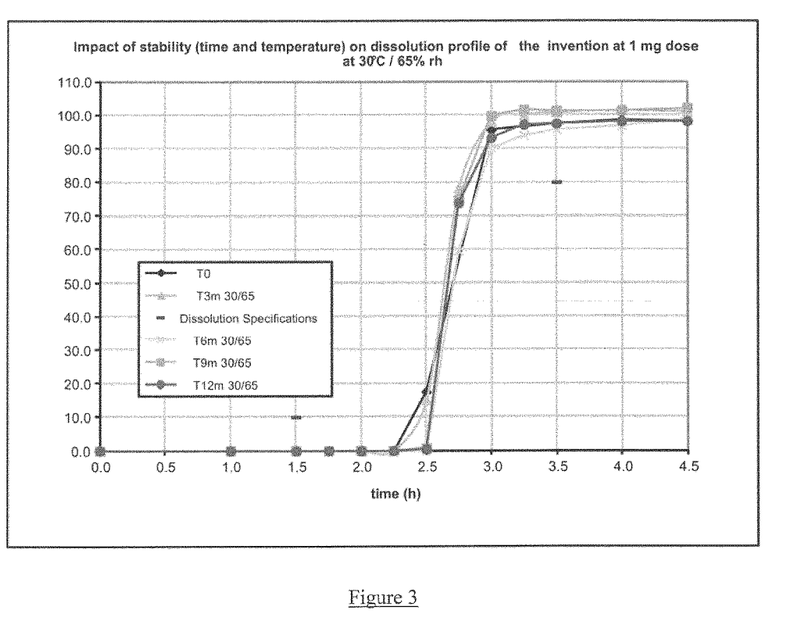
FIG. 3: Mean dissolution profiles of press coated tablets prepared according to Example 1 following storage at 30° C./65% RH.

Mean (N=6) dissolution profiles of 1 mg terbutaline sulphate press coated tablets prepared according to Example 1 and stored at 30° C./65%' in HDPE bottles are presented in FIG. 3. The dissolution test is conducted in USP apparatus II with stationary baskets at 100 rpm paddle speed in 500 ml of water. Collected fractions are analysed by HPLC.

EXAMPLE 6

Figure 4:
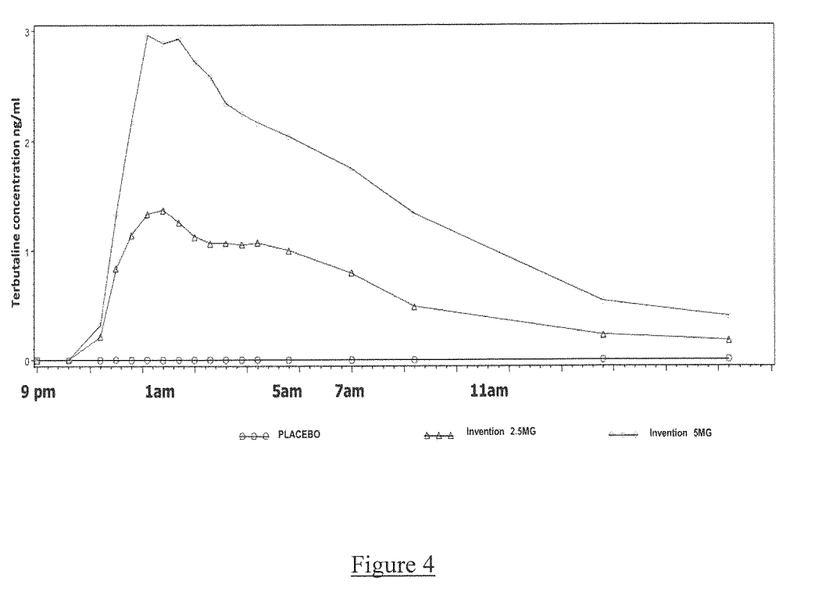
FIG. 4: Terbutaline plasma concentrations in patients with type 1 diabetes mellitus (T1DM) in a randomized, single blind, cross-over study.
Figure 5:
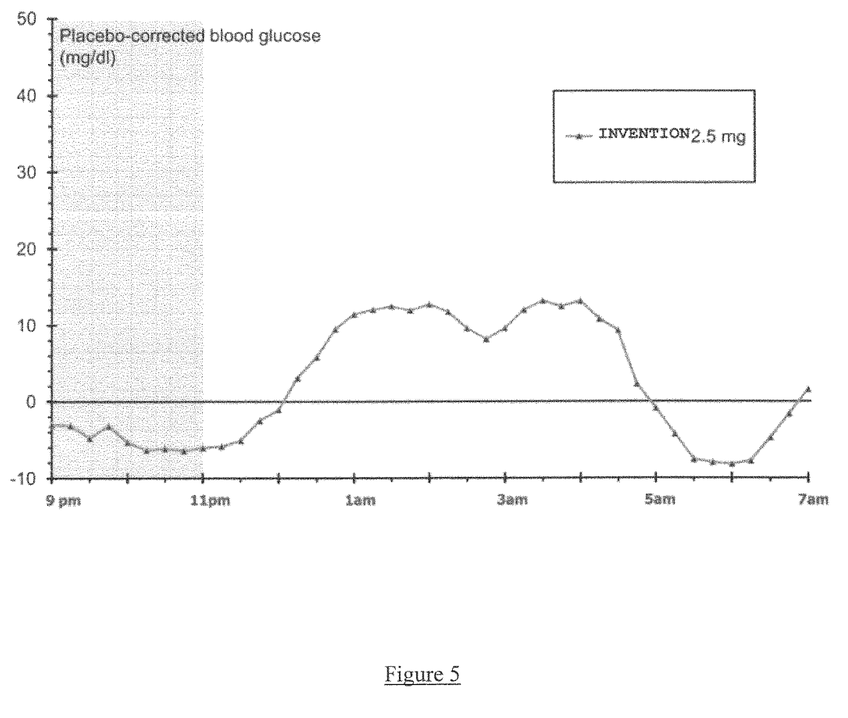
FIG. 5: Blood glucose concentrations in patients in a randomized, single blind, corss-over study.

Formulations prepared according to the invention are dosed at bedtime in patients with type 1 diabetes mellitus (T1DM). In a randomized, single blind, cross-over study the invention terbutaline sulphate formulations at 2.5 and 5 mg doses are compared with placebo on overnight blood glucose and terbutaline plama concentration profiles in 30 persons with T1DM. After stabilization of blood glucose concentrations at 90 mg/dL (5 mmol/l) with an isoglycaemic glucose clamp technique subjects receive a standardized evening meal preceeded by s.c. injections of individualized doses of insulin glargine. The study medications are administered around 9 pm. Terbutaline concentrations (FIG. 4) and blood glucose (FIG. 5) are monitored overnight.

Formulations according to the invention achieved a delayed onset in terbutaline concentrations (tmax [mean±SD] 5.0±2.1 h (2.5 mg) and 4.7±1.7 h (5 mg), they achieved a mean Cmax of 3.82 ng/ml and 1.74 ng/ml respectively for the 5 mg and 2.5 mg doses.

The invention claimed is:

1. An oral dosage form containing terbutaline sulphate, said dosage form comprising
an internal phase of particles of terbutaline sulphate coated with or surrounded by particles of a single pharmaceutically acceptable excipient selected from a diluent,
said particles being dispersed in an external phase comprising particles of one or more additional pharmaceutically acceptable excipients, and wherein the internal phase comprises less than 25% by weight of terbutaline sulphate.

2. An oral dosage form according to claim 1 in the form of a tablet.

3. An oral dosage form according to claim 1 comprising 0.1 to 10% by weight of terbutaline sulphate.

4. An oral dosage form according to claim 1 wherein the internal phase comprises 1 mg, 2.5 mg or 5 mg of terbutaline sulphate.

5. An oral dosage form according to claim 1 wherein the internal phase and external phase together form a core, which core is covered by a coating.

6. An oral dosage form according to claim 5 wherein the coating is formed by press-coating.

7. An oral dosage form according to claim 1 wherein the diluent is selected from the group consisting of lactose monohydrate, dibasic calcium phosphate, dehydrate, xylitol and microcrystalline cellulose.

8. An oral dosage form according to claim 1, wherein the internal phase contains from about 3.7% to about 18.4% by weight of terbutaline sulphate.

9. An oral dosage form according to claim 1 wherein the one or more pharmaceutically acceptable excipients of the external phase is selected from a diluent selected from lactose monohydrate, dibasic calcium phosphate, dehydrate, xylitol or microcrystalline cellulose; a binder; a surfactant; a disintegrant croscarmellose sodium, pre-gelatinised starch, or crospovidone; a flow agent; a lubricant; a permeability regulator; a colouring agent; a chelating agent; a solubiliser; and an anti-oxidant selected from ascorbic acid, citric acid, malic acid, tartaric acid, sodium metabisulphite, meglumine, tromethamine or butylhydroxytoluene.

10. An oral dosage form according to claim 4 having 1 mg tertbutaline sulphate in the internal phase and comprising no more than 1% by weight of terbutaline impurity B based on the total dose of terbutaline sulphate when subjected to stress testing for 3 to 6 months at 40° C. and 75% relative humidity.

11. An oral dosage form according to claim 1 adapted to release terbutaline sulphate after a lag time of one to three hours after ingestion or immersion in a simulated physiological medium.

12. An oral dosage form according to claim 1, which when tested in a group of human subjects achieves for a 5 mg dose of terbutaline sulphate, a mean peak plasma terbutaline concentration (Cmax) of about 2.5 to 5 ng/ml.

13. An oral dosage form according to claim 1, which when tested in a group of human subjects achieves for a dose of 2.5 mg terbutaline sulphate a mean peak plasma terbutaline concentration of about 1.0 and 2.5 ng/ml.

14. An oral dosage form according to claim 1 wherein when tested in a group of human subjects provides a time ($T_{max}$) to mean peak plasma concentration ($C_{max}$) between 1 hour and 6 hours of administration of said dosage form, more particularly between 1 to 3 hours of administration of said dosage form.

15. A method of treating nocturnal hypoglycaemia comprising the step of administering to a patient in need of treatment the oral dosage form of claim 1.

16. The method of claim 15, wherein the method prevents or reduces the incidence of hyperglycaemia in said subjects upon wakening.

17. The method of claim 15, wherein the method minimizes or avoids adverse events including incidences of hyperglycaemia in the treated subjects upon wakening and/or worsening glucose control.

18. A treatment regimen for treating nocturnal hypoglycaemia comprising administering the oral dosage form of claim 1 once a day before bedtime either simultaneously with food or after food.

19. The method of claim 15 further comprising the steps of (a) determining if said patient is undergoing treatment with one or more first medications and (b) administering a dosage form as defined herein to said patient based on said patient's treatment with said one or more first medications.

20. The method of claim 19 wherein said first medication is selected from the group consisting of insulin or other antidiabetic medications including oral hyperglycaemic agents, ethanol, Beta blockers, e.g. propranolol, salicylates, Acetaminophen, Acetazolamide, Aluminium hydroxide, Chloroquine, Chlorpromazine, Cimetidine, Ranitidine, Diphenhydramine, Propoxyphene, Disopyramide, Doxepin, Isoxsuprine, Insulin-like growth factor 1, Lidocaine, Lithium, Pentamidine, Propranolol, nadolol, labetalol, metoprolol, Orphenadrine, Oxytetracycline, Quinine, quinidine, Perhexiline, Ritodrine, Haloperidol, Chelating agents, Colchicine, Para amino benzoic acid, para-amino salicylic acid, Cholestyramine added during glucocorticoid therapy (reduces absorption), Drugs which lower glucose in diabetics mentioned above, Enalapril and captopril, Coumarin, Phenylbutazone, Antihistamines, Sulfa antibiotics, Monoamine oxidase inhibitors, Azapropazone, buformin, carbutamide, cibenzoline, cycloheptolamide, glibornuride, gliclazide, mebanazine, metahexamide, perhexiline, sulphadimidine and sulphaphenazole.

21. A method for stabilizing an oral dosage form comprising terbutaline sulphate and pharmaceutically acceptable excipients, said method comprising the steps of:
i) admixing 1 to 5 mg of terbutaline sulphate with a single pharmaceutically acceptable excipient selected from a diluent to form a first internal phase of particles of terbutaline sulphate and the excipient,
ii) optionally mixing the particles of step 1 with an optional second internal phase comprising one or more additional pharmaceutically acceptable excipients but no terbutaline sulphate,
iii) mixing the particles of the first internal phase and the optional second internal phase with an external phase comprising one or more pharmaceutically acceptable excipients but no terbutaline sulphate, and
iv) forming the mixture resulting from step iii) into an oral dosage form.

22. The method of claim 21, wherein step ii) is performed.

23. The method of claim 21, wherein the particles in step i) are formed by wet granulation.

24. The method of claim 21, wherein the particles in step i) consist of terbutaline sulphate and lactose monohydrate.

25. A dosage form obtained by the method of claim 21.

26. The regimen of claim 18, further comprising the steps of (a) determining if said patient is undergoing treatment with one or more first medications and (b) administering a dosage form as defined herein to said patient based on said patient's treatment with said one or more first medications.

27. The regimen of claim 19, wherein said first medication is selected from the group consisting of insulin or other antidiabetic medications including oral hyperglycaemic agents, ethanol, Beta blockers, e.g. propranolol, salicylates, Acetaminophen, Acetazolamide, Aluminium hydroxide, Chloroquine, Chlorpromazine, Cimetidine, Ranitidine, Diphenhydramine, Propoxyphene, Disopyramide, Doxepin, Isoxsuprine, Insulin-like growth factor 1, Lidocaine, Lithium, Pentamidine, Propranolol, nadolol, labetalol, metoprolol, Orphenadrine, Oxytetracycline, Quinine, quinidine, Perhexiline, Ritodrine, Haloperidol, Chelating agents, Colchicine, Para amino benzoic acid, para-amino salicylic acid, Cholestyramine added during glucocorticoid therapy (reduces absorption), Drugs which lower glucose in diabetics mentioned above, Enalapril and captopril, Coumarin, Phenylbutazone, Antihistamines, Sulfa antibiotics, Monoamine oxidase inhibitors, Azapropazone, buformin, carbutamide, cibenzoline, cycloheptolamide, glibornuride, gliclazide, mebanazine, metahexamide, perhexiline, sulphadimidine and sulphaphenazole.

\* \* \* \* \*